US012533458B2

(12) United States Patent
Maaskamp et al.

(10) Patent No.: US 12,533,458 B2
(45) Date of Patent: Jan. 27, 2026

(54) CANNULA WITH RETRACTING FLEXIBLE TIP

(71) Applicants: Ryan Maaskamp, Scottsdale, AZ (US); Armand Maaskamp, Scottsdale, AZ (US); Dan Thompson, Irvine, CA (US)

(72) Inventors: Ryan Maaskamp, Scottsdale, AZ (US); Armand Maaskamp, Scottsdale, AZ (US); Dan Thompson, Irvine, CA (US)

(73) Assignee: SURGIN, INC., Scottsdale, AZ (US)

( * ) Notice: Subject to any disclaimer, the term of this patent is extended or adjusted under 35 U.S.C. 154(b) by 120 days.

(21) Appl. No.: 18/415,846

(22) Filed: Jan. 18, 2024

(65) Prior Publication Data

US 2025/0235597 A1 Jul. 24, 2025

(51) Int. Cl.

| | |
|---|---|
| ***A61M 1/00*** | (2006.01) |
| ***A61M 25/00*** | (2006.01) |
| ***A61M 25/06*** | (2006.01) |

(52) U.S. Cl.

CPC .............. *A61M 1/77* (2021.05); *A61M 1/772* (2021.05); *A61M 1/774* (2021.05); *A61M 1/85* (2021.05); *A61M 2025/0004* (2013.01); *A61M 25/0054* (2013.01); *A61M 2025/0681* (2013.01)

(58) Field of Classification Search

CPC ........ A61M 1/77; A61M 1/772; A61M 1/774; A61M 1/85; A61M 2025/0004; A61M 2025/0006; A61M 25/0054; A61M 25/0053; A61M 2210/1021; A61M 1/777; A61M 25/0041; A61M 2025/0063; A61M 25/0067; A61M 25/0068; A61M 25/008; A61M 2025/0081; A61M 2025/0098; A61M 2025/0175; A61M 25/0662; A61M 2025/0681; A61M 25/0133; A61M 25/0138; A61M 25/0152; A61B 17/3421

See application file for complete search history.

(56) References Cited

U.S. PATENT DOCUMENTS

2010/0010524 A1* 1/2010 Barrington ......... A61B 17/3203 606/167
2010/0185053 A1 7/2010 Hagen
2014/0142497 A1* 5/2014 Esposito ................. A61M 1/77 156/196
2015/0012008 A1* 1/2015 Mcweeney ........ A61B 10/0283 606/108

(Continued)

*Primary Examiner* — Kami A Bosworth
*Assistant Examiner* — Avery Smale
(74) *Attorney, Agent, or Firm* — Kenneth Altshuler

(57) ABSTRACT

A cannula to access the deep pelvic space of a patient from an incision near a patient's navel, wherein the deep pelvic space is generally inaccessible from the incision due to being obstructed by the patient's sacral promontory. The cannula is envisioned having an inner tube that slides within a rigid outer tube. The inner tube has a suction-irrigation tip located at the distal tube end and a flexible tube section interposed between the suction-irrigation tip and a rigid inner tube, which extends from the flexible tube section, outside of the proximal end of the rigid outer tube, where it is attached to a handle. The handle has an exit port centered in the handle (in communication with the suction-irrigation tip aperture), which is configured to suck fluid buildup in the deep pelvic space when the exit port is connected to a suction source via a suction tube.

20 Claims, 12 Drawing Sheets

(56) References Cited

U.S. PATENT DOCUMENTS

| | | | | |
|---|---|---|---|---|
| 2015/0290426 | A1 * | 10/2015 | Rasmussen ......... | A61M 25/005 604/513 |
| 2019/0321019 | A1 * | 10/2019 | Novell .................... | A61M 1/77 |

* cited by examiner

CANNULA WITH RETRACTING FLEXIBLE TIP

CROSS-REFERENCE TO RELATED APPLICATIONS

None.

FIELD OF THE INVENTION

The present embodiments are generally directed to a suction-irrigation cannula with an optionally flexible distal tube.

DESCRIPTION OF RELATED ART

Laparoscopic surgery is a minimally invasive surgical procedure that offers a number of advantages to a patient over conventional exploratory laparotomy. For example, patients that undergo laparoscopic surgery generally experience reduced pain due to smaller incisions, reduced hemorrhaging and shorter recovery time. Laparoscopic surgery employs a laparoscope that facilitates viewing of other instruments, such as cutting tools, graspers, irrigation and suction tubes, probes, dissectors, hooks, retractors, etc., that are manipulated in a person's abdomen or pelvic region. A laparoscope is a long fiber optic cable system that is inserted through a 5-10 mm cannula or trocar. A laparoscope provides a real-time visual of an affected area by snaking or otherwise weaving the optical cable from a distant, but easily accessible location, from a small incision on the patient, such as at or just below or above a person's navel.

Typically, during laparoscopic surgery, 3-6 laparoscopic incisions are made in the patient's abdomen for tools to access the affected area. Air is generally used to distend the patient's abdomen to better visualize the organs being worked on. One problem encountered with laparoscopic surgery is fluid pooling in the cupped region of the coccyx, known as the deep pelvic space, which can occur while the patient is lying on their back during a procedure. Though it would be desirable to suck the fluid out from the deep pelvic space with a rigid suction-irrigation cannula via a pre-existing incision already at or in proximity of the patient's navel, it is highly difficult to impossible to do so because the sacral promontory obstructs access to the deep pelvic space. Accordingly, another incision must be made lower in the patient's abdomen to access the deep pelvic space via the rigid suction cannula to suck fluid therefrom. The upside to another incision is that it is fairly simple, and the added incision offers another port of entry if needed for other instruments or the rapid redeployment of the rigid suction cannula without removing the instrument already in the pre-existing incision. The downside of this is that every incision made in the patient's abdomen takes time, exposes the patient to potential infections and generally adds to the complexity of the surgery and recovery.

It is to improvements to accessing the deep pelvic space that the claimed invention is generally directed.

SUMMARY OF THE INVENTION

The present embodiments are generally directed to a suction-irrigation cannula with an optionally flexible distal tube that is configured to arc around a patient's sacral promontory to access the patient's deep pelvic space.

Accordingly, certain embodiments contemplate a cannula comprising a rigid outer tube defined between an inlet port and an outlet port, wherein a central axis extends concentrically through the inlet port and the outlet port. An inner tube, which is defined between a proximal tube end and a distal tube end comprises a suction-irrigation tip located at the distal tube end and a flexible tube section interposed between the suction-irrigation tip and a rigid inner tube segment. The rigid inner tube segment extends from the flexible tube section to the proximal tube end. The cannula further comprises a hub, which can be used as a handle, attached to the proximal tube end, wherein the hub comprising a hub aperture that is centered in the central axis. The hub aperture is in communication with an aperture in the suction-irrigation tip. The inner tube slidingly engaged inside of the rigid outer tube, wherein the suction-irrigation tip and the hub are never in the rigid outer tube.

Yet other embodiments of the present invention contemplate a method comprising providing a cannula that has a rigid outer tube defined between an inlet port and an outlet port that sleeves over an inner tube defined between a proximal tube end and a distal tube end. The cannula defines a central axis centered through the inlet port and the outlet port. The inner tube has a suction-irrigation tip located at the distal tube end and a flexible tube section interposed between the suction-irrigation tip and a rigid inner tube segment. The rigid inner tube segment is attached to a hub at the proximal tube end. The hub comprises a hub aperture that is centered in the central axis. While the inner tube is fully retracted in the outer tube with the suction-irrigation tip abutting the outlet port, the suction-irrigation tip is inserted until it reaches a sacral promontory of a person. This is accomplished via a laparoscopic incision that is from between 2 inches below a navel to a location above the navel. The method further envisions extending at least a portion of the flexible tube section from the outlet port by moving the hub towards the inlet port. Next the suction-irrigation tip is directed away from the central axis by bending the flexible tube section around the sacral promontory to a deep pelvic region of the person.

Still, other embodiments of the present invention envision a method for deploying a cannula in a person. The method comprising providing the cannula having an inner tube defined between a proximal tube end and a distal tube end that is slidingly engaged in a rigid outer tube, which is defined between an inlet port and an outlet port. A central axis is centered through the inlet port and the outlet port. The inner tube comprises a suction-irrigation tip that is located at the distal tube end and a flexible tube section extending towards the proximal tube end. A hub is attached to the proximal tube end, wherein the hub comprising a hub aperture. The suction-irrigation tip is inserted to a sacral promontory of the person via a laparoscopic incision that is between 2 inches below the patient's navel to 2 inches above a patient's navel towards the patient's head. Optionally, the incision is 2 inches below the patient's navel to all distal areas or locations above the navel (towards the patient's head). During this step, the inner tube is fully retracted in the outer tube. The suction-irrigation tip abuts the outlet port when the inner tube is fully retracted in the outer tube. At least a portion of the flexible tube section is extended or otherwise protracted from the outlet port by pushing the hub towards the inlet port. The suction-irrigation tip is directed away from the central axis either via a force external to the cannula or by bending the flexible tube section around the sacral promontory to a deep pelvic region of the person. When in the person, the inner tube never contains material other than that consisting of gas, irrigation fluid, bodily fluid or bodily tissue. In certain embodiments, the suction-irrigation tip is cylindrical and has an outer suction-irrigation tip diameter that is equal to an outer tube diameter of the rigid outer tube.

DETAILED DESCRIPTION

Figure 1:
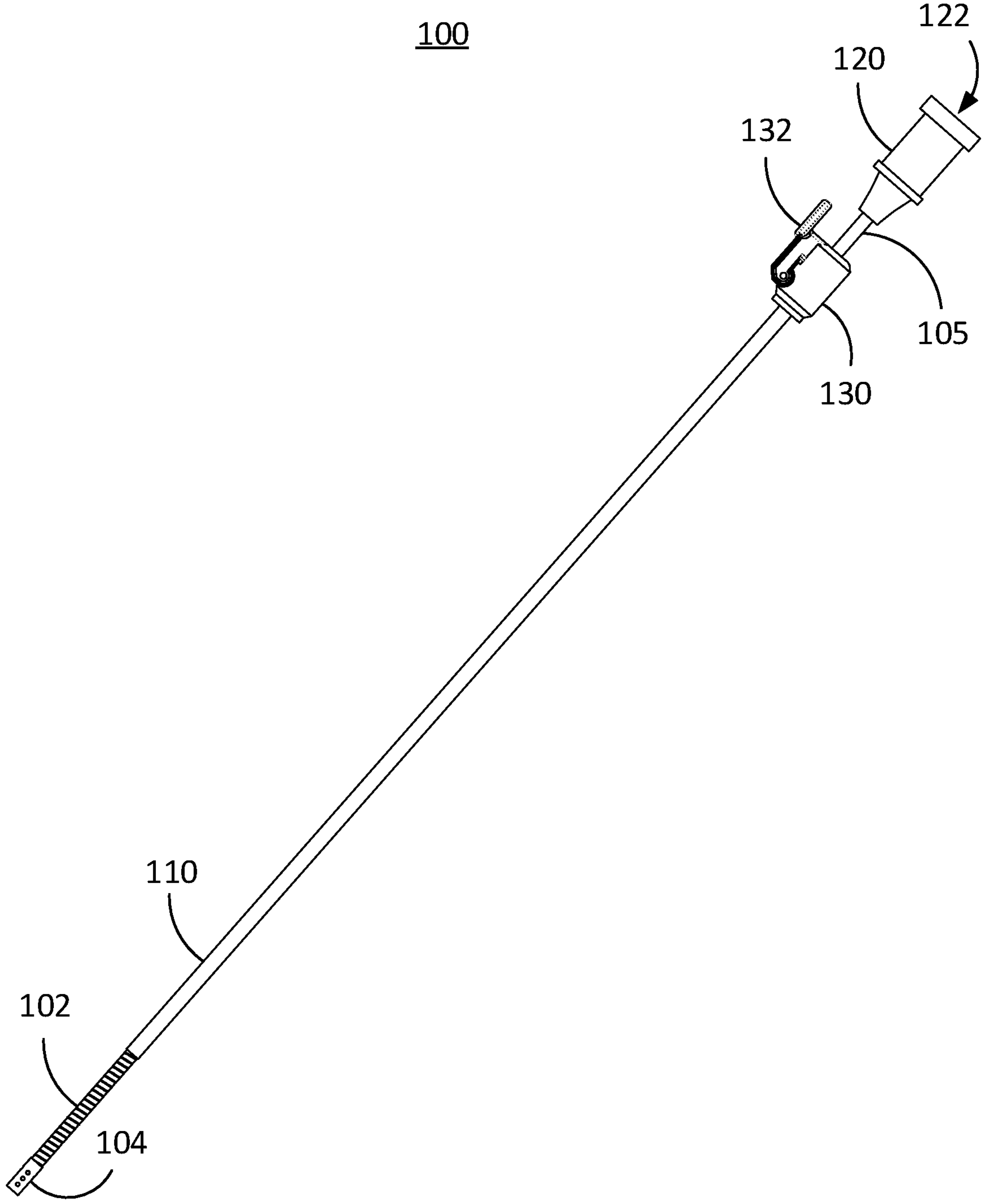
FIG. 1 is a side view line drawing of cannula embodiment that exemplifies certain inventive aspects of the present invention.

Initially, this disclosure is by way of example only, not by limitation. Thus, although the instrumentalities described herein are for the convenience of explanation, shown and described with respect to exemplary embodiments, it will be appreciated that the principles herein may be applied equally in other similar configurations involving the subject matter directed to the field of the invention. The phrases "in one embodiment", "according to one embodiment", and the like, generally mean the particular feature, structure, or characteristic following the phrase, is included in at least one embodiment of the present invention and may be included in more than one embodiment of the present invention. Importantly, such phases do not necessarily refer to the same embodiment. If the specification states a component or feature "may", "can", "could", or "might" be included or have a characteristic, that particular component or feature is not required to be included or have the characteristic. As used herein, the terms "having", "have", "including" and "include" are considered open language and are synonymous with the term "comprising". Furthermore, as used herein, the term "essentially" is meant to stress that a characteristic of something is to be interpreted within acceptable tolerance margins known to those skilled in the art in keeping with typical normal world tolerance, which is analogous with "more or less." For example, essentially flat, essentially straight, essentially on time, etc. all indicate that these characteristics are not capable of being perfect within the sense of their limits. Accordingly, if there is no specific +/− value assigned to "essentially", then assume essentially means to be within +/−2.5% of exact. The term "connected to" as used herein is to be interpreted as a first element physically linked or attached to a second element and not as a "means for attaching" as in a "means plus function". In fact, unless a term expressly uses "means for" followed by the gerund form of a verb, that term shall not be interpreted under 35 U.S.C. § 112(f). In what follows, similar or identical structures may be identified using identical callouts.

With respect to the drawings, it is noted that the figures are not necessarily drawn to scale and are diagrammatic in nature to illustrate features of interest. Descriptive terminology such as, for example, upper/lower, top/bottom, horizontal/vertical, left/right and the like, may be adopted with respect to the various views or conventions provided in the figures as generally understood by an onlooker for purposes of enhancing the reader's understanding and is in no way intended to be limiting. All embodiments described herein are submitted to be operational irrespective of any overall physical orientation unless specifically described otherwise, such as elements that rely on gravity to operate, for example.

The present embodiments are directed to cannula embodiments that are configured to access a patient's deep pelvic space from an incision in a person's abdomen, which in some embodiments is near or at a patient's navel. The deep pelvic space is generally inaccessible to a standard linear cannula/tube from the incision near or at the patient's navel due to being obstructed by the patient's sacral promontory. The cannula is envisioned to comprise an inner tube that slides within a rigid outer tube. The inner tube has a suction-irrigation tip located at the distal tube end and a flexible tube section that is interposed between the suction-irrigation tip and a rigid inner tube segment. The rigid inner tube segment extends from the flexible tube section, outside of the proximal end of the rigid outer tube, where the proximal end of the rigid inner tube segment is attached to a hub, which can be used as a handle grasped by a human hand. The hub has an exit port, that is centered in the hub. The exit port is in communication with an aperture in the suction-irrigation tip, which is configured to suck fluid buildup in the deep pelvic space when the exit port is connected to a suction source via a suction tube. The suction-irrigation tip and the hub are never in the rigid outer tube.

FIG. 1 is a side view line drawing of cannula embodiment that exemplifies certain inventive aspects of the present invention. As shown, the cannula embodiment 100 generally includes a rigid outer tube 110 that sleeves around (i.e., acts as a sleeve) over an inner tube 105. The inner tube 105 can be manipulated to slide through the rigid outer tube 110 via a handle/hub 120 to expose or otherwise deploy a flexible tube section 102 that is part of the inner tube 105. This cannula embodiment 100 is equipped with a lock-and-release switch 130 that can lock the flexible tube section 102 at a desired extension length (outside of the rigid outer tube 110) via a lock-and-release actuator arm 132. The present cannula embodiment 100 further comprises a suction-irrigation tip 104 that is equipped to suck (or optionally dispense) fluid through the inner tube 102 and out through a hub aperture/port 122 in the hub 120.

Figure 2:
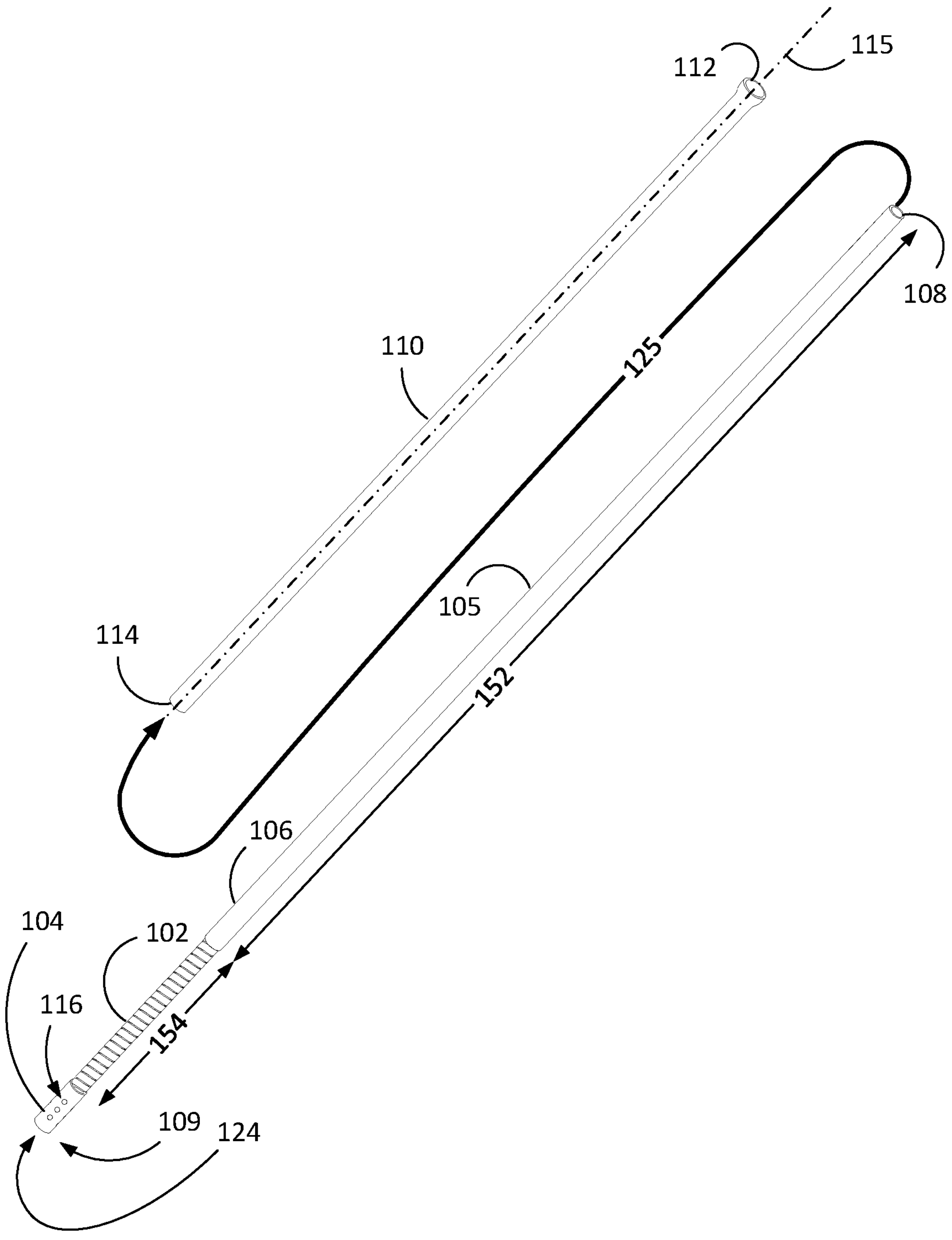
FIG. 2 is a line drawing of the relationship between the inner tube and the outer tube consistent with embodiments of the present invention.

FIG. 2 is a line drawing of the relationship between the inner tube 105 and the outer tube 110 consistent with embodiments of the present invention. With respect to the inner tube embodiment 105, the main elements include a suction-irrigation tip 104 located at the distal tube end 109 and a flexible tube section 102 interposed between the suction-irrigation tip 104 and a rigid inner tube segment 106. The rigid inner tube segment 106 extends from the flexible tube section 102 to a proximal tube end 108. The rigid inner tube segment 106 has a rigid inner tube segment length 152 that is longer than the flexible tube segment length 154 of the flexible tube 102. In some embodiments, the rigid inner tube segment length 152 is more than 50% of the length of the combined flexible tube segment length 154 and the rigid inner tube segment length 152. Certain other embodiments envision the flexible tube segment length 154 being up to 80% of the entire inner tube length. The suction-irrigation tip 104 can include a plurality of suction-irrigation tip apertures 116 and/or a main suction-irrigation tip port 124 extending through the distal tip 109 of the suction-irrigation tip 104.

The rigid outer tube 110 is defined between an inlet port 112 and an outlet port 114. In this embodiment, the inlet port 112 is flared to provide a seal when fixedly attached within the inner tube lock-and-release switch 130. For reference, the rigid outer tube 110 defines a central axis 115 extending through its center, i.e., through the center of the inlet port 112 and the outlet port 114. As shown by the curved arrow 125, the inner tube 105 slidingly engages the inside of the rigid outer tube 110, wherein the rigid outer tube and the rigid inner tube segment 106 commonly share the central axis 115.

Figure 3A:
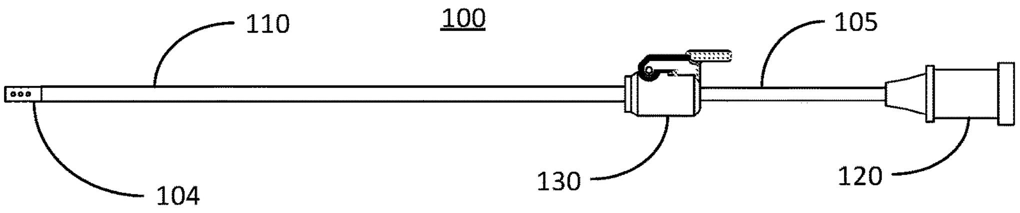
FIGS. 3A-3C are various side view line drawings of the cannula embodiment consistent with embodiments of the present invention.
Figure 3B:
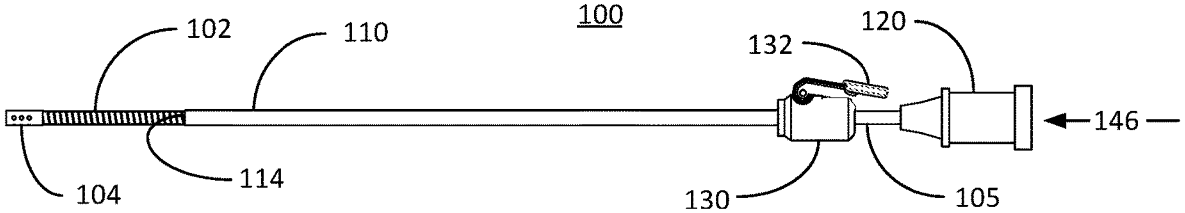
Figure 3C:
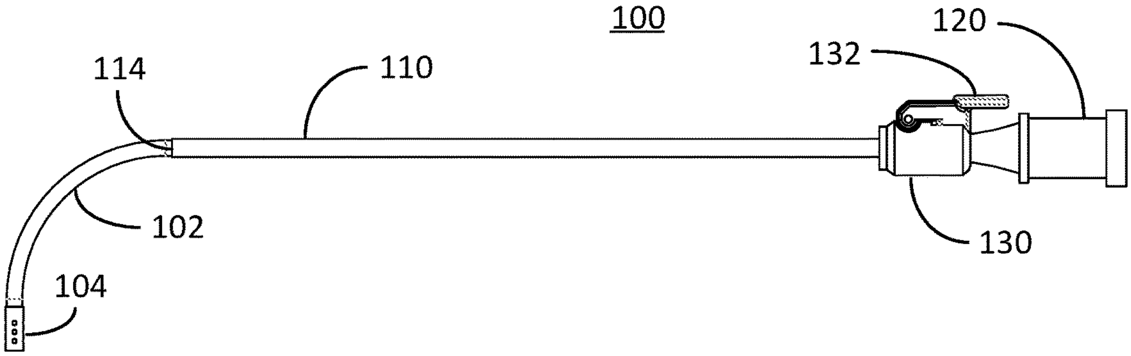

FIGS. 3A-3C are various side view line drawings of the cannula embodiment 100 consistent with embodiments of the present invention. FIGS. 3A and 3B illustratively depict the rigid outer tube 110 aligned to show the movement of the inner tube 105 relative to the rigid outer tube 110. FIG. 3A depicts the cannula embodiment 100 in a fully retracted orientation with the suction-irrigation tip 104 abutting or otherwise in contact with the rigid outer tube 110. In this orientation, the inner tube 105 is maximally extending in the distal direction from the inner tube lock-and-release switch 130, which locks the inner tube 105 in the retracted orientation. During a laparoscopic procedure, the cannula embodiment 100 is envisioned to be inserted in an incision while in the retracted orientation.

FIG. 3B illustratively depicts the inner tube 105 at least partially protracted from the rigid outer tube 110. In this protracted orientation, the flexible tube section 102 is at least partially extended from the rigid outer tube 110. During a laparoscopic procedure, the cannula embodiment 100 is envisioned to already be inserted up to or near (within 1 inch) the sacral promontory 210 (of FIG. 6A) while in the fully retracted orientation before deploying the flexible tube section 102. In this embodiment, the actuator arm 132 of the inner tube lock-and-release switch 130 is depressed thereby freeing, or unlocking, the inner tube 105 to slide inside of the rigid outer tube 110. Hence, with the inner tube 105 unlocked, the hub 120 is pushed in the direction of the arrow 146, which extends, or deploys, the flexible tube section 102 from the outlet port 114 of the rigid outer tube 110.

FIG. 3C illustratively depicts the inner tube 105 fully protracted from the rigid outer tube 110 and bent away from the central axis 115 with the hub 120 in contact with the inner tube lock-and-release switch 130 (or optionally as far as the hub 120 can move to the left). In the protracted orientation, the flexible tube section 102, which is at least partially extended from the rigid outer tube 110, can be bent around the sacral promontory 210 towards the deep pelvic space 212 (of FIG. 6B). In this embodiment, it is envisioned that the actuator arm 132 of the inner tube lock-and-release switch 130 is released thereby locking the inner tube 105 in position inside of the rigid outer tube 110. Certain embodiments contemplate the minimum radius of the flexible tube section 102 having a radius of 0.86 inches with the suction-irrigation tip 104 pointing down at 90 degrees from the rigid outer tube 110. Other embodiments contemplate not being subject to this minimum radius.

Figure 3D:
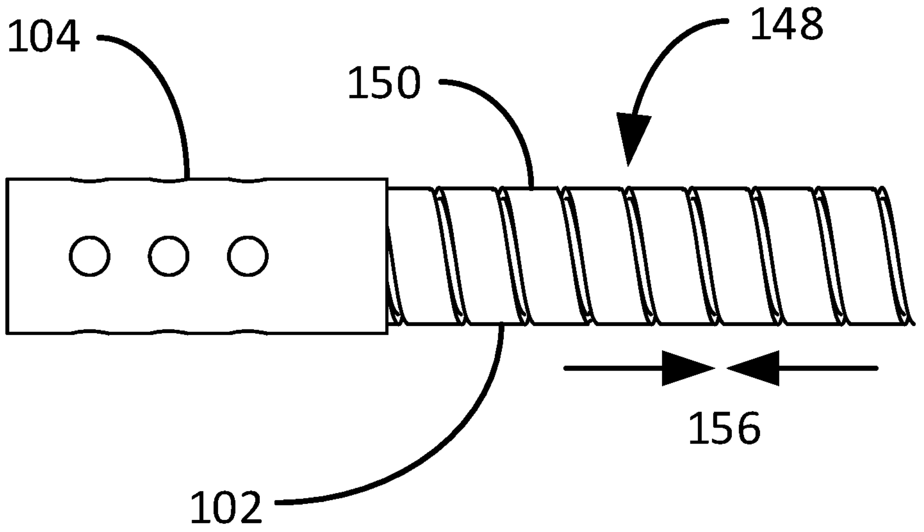
FIG. 3D is a line drawing illustratively depicting the flexible tube section and suction-irrigation tip at a higher resolution.

FIG. 3D is a line drawing illustratively depicting the flexible tube section 102 and suction-irrigation tip 104 at a higher resolution to better show the spiral cut 148 that provides flexibility of the flexible tube section 102. In this embodiment, the rigid inner tube segment 106 is cut with spiral through-cuts 148 that extend from the flexible tube outer surface 150 of the flexible tube section 102 through to the flexible tube inner surface (not shown) of the flexible tube section 102. The spiral cut 148 comprises a clearance 156 of about 1 mm, which allows movement, or flexibility, of the flexible tube section 102. The clearance 156 can be other dimensions depending on how much movement is desired in the flexible tube section 102. Certain embodiments envision the flexible tube section 102 and the rigid inner tube segment 106 being coated with Teflon, which is envisioned to cover the spiral cut 148. The Teflon adds a more frictionless interface between the inner tube 105 and the rigid outer tube 110 when the inner tube slides within the rigid outer tube 100. Other embodiments imagine a flexible polymer sleeve (not shown) fitted over and perhaps shrunken on the flexible tube section 102 to seal the spiral cut 148 so that there is no communication from inside the inner tube 105 to the outside 150 of the inner tube 105 via the spiral cut 148. Still other embodiments envision a flexible tube section 102 that is constructed with any number or flexible tube configurations known to those skilled in the art that is attached to the rigid inner tube segment 106. The suction-irrigation tip 104 is attached to the distal end of the flexible tube section 102, such as via adhesive, a screw-on fit, press fit, etc.

Figure 3E:
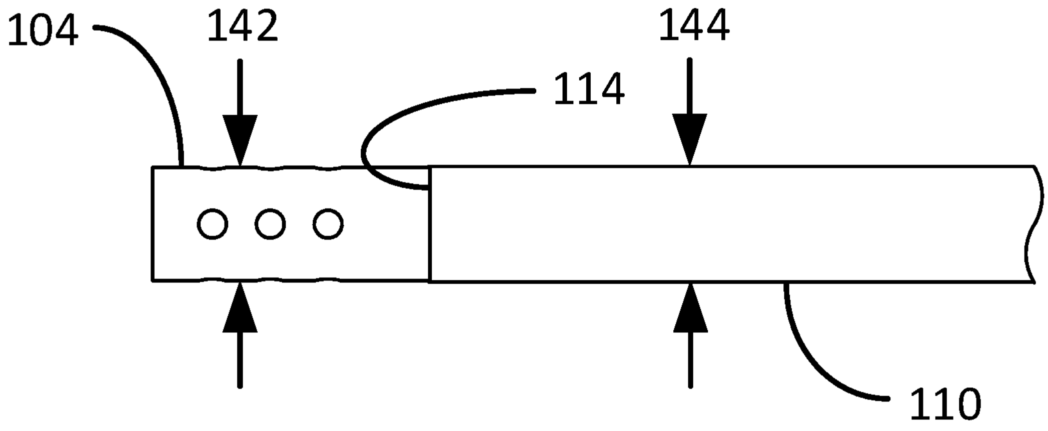
FIG. 3E is a line drawing illustratively depicting the suction-irrigation tip butting up against the outlet port of the rigid outer tube.

FIG. 3E is a line drawing illustratively depicting the suction-irrigation tip 104 butting up against the outlet port 114 of the rigid outer tube 110. This embodiment envisions the outer suction-irrigation tip diameter 142 being essentially identical to the outer tube diameter 144 in order to provide a smooth entry of the suction-irrigation tip 104 and rigid outer tube 110 into the patient 200. Also, in this embodiment the suction-irrigation tip 104 and rigid outer tube 110 (as well as the flexible tube section 102 and rigid inner tube segment 104) are cylindrical elements with a circular cross-section.

Figure 4A:
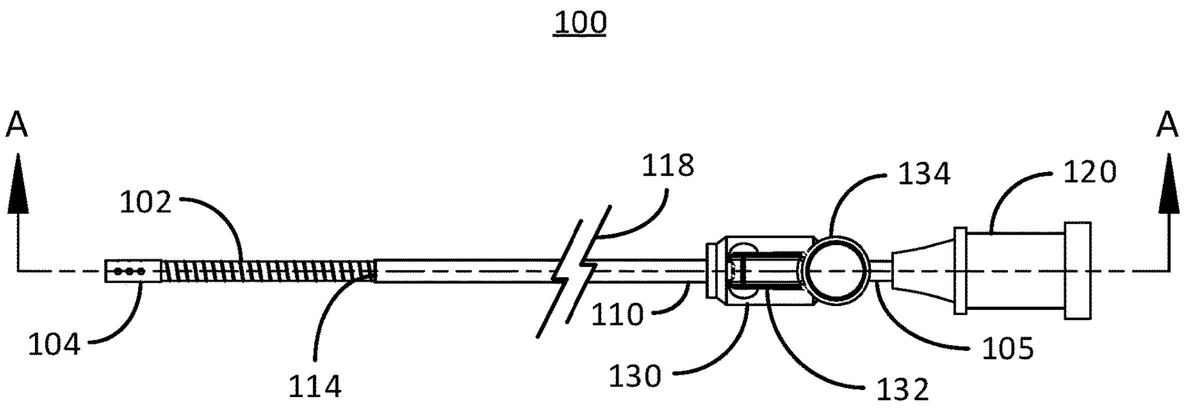
FIGS. 4A and 4B are line drawings of a cross-section view of the cannula embodiment consistent with embodiments of the present invention.
Figure 4B:
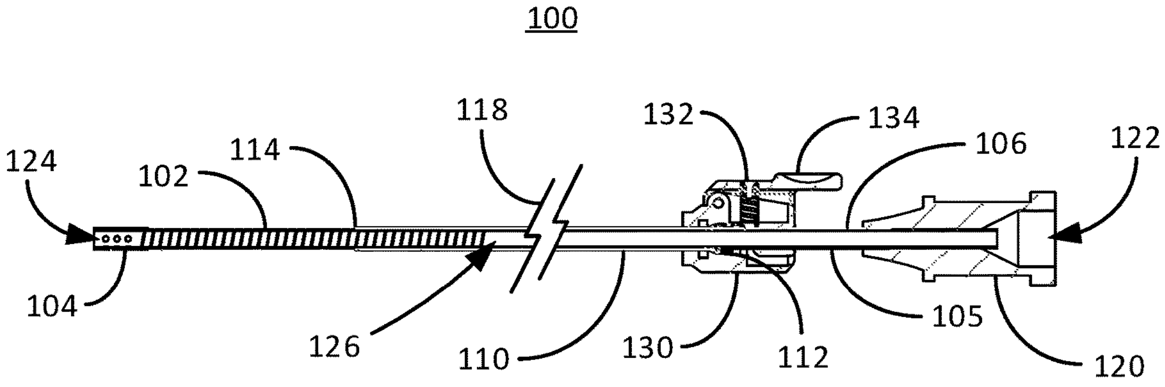

FIGS. 4A and 4B are line drawings of a cross-section view of the cannula embodiment 100 consistent with embodiments of the present invention. FIG. 4A is a top view of the cannula embodiment 100 with a section line A-A bisecting the inner tube 105, the rigid outer tube 110, the hub 120 and the inner tube lock and release 130. There is a cutline 118 that compresses the cannula embodiment 100 along the rigid outer tube 110, as shown. Certain embodiments envision the length of the cannula embodiment 100 being between 10-24 inches long and the width being between 5-10 mm. From this perspective, a circular depression platform 134 is depicted at the end of the actuator arm 132 of the inner tube lock and release 130. The circular depression platform 134 configured to be depressed via the tip of a user's thumb, wherein when circular depression platform 134 is depressed, the inner tube 105 is released to freely move/slide within the rigid outer tube 110. Here, the suction-irrigation tip 104 and the flexible tube section 102 are in a partially protracted orientation.

FIG. 4B is the cross-section view of the cannula embodiment 100 along section line A-A consistent with embodiments of the present invention. As shown, there is an uninterrupted passageway 126 between a distal cannula port 124 and a proximal hub exit port 122, wherein the distal cannula port 124 and the proximal hub exit port 122 are in communication. Also, as shown, the rigid inner tube segment 106 is fixedly captured inside of the hub 120 and the rigid outer tube 110 is fixedly captured inside of the inner tube lock-and-release switch 130 at the rigid two inlet port 112.

Figure 5A:
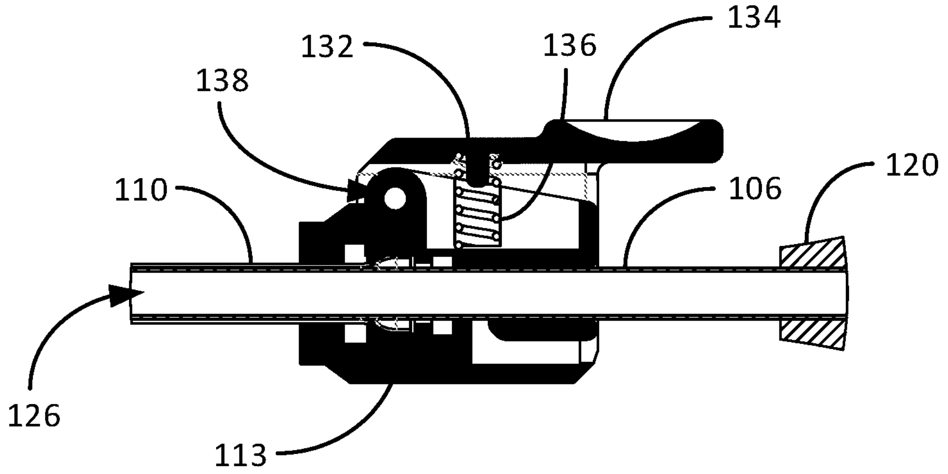
FIGS. 5A and 5B are cross-section view line drawings of the inner tube lock-and-release switch along section line A-A consistent with embodiments of the present invention.
Figure 5B:
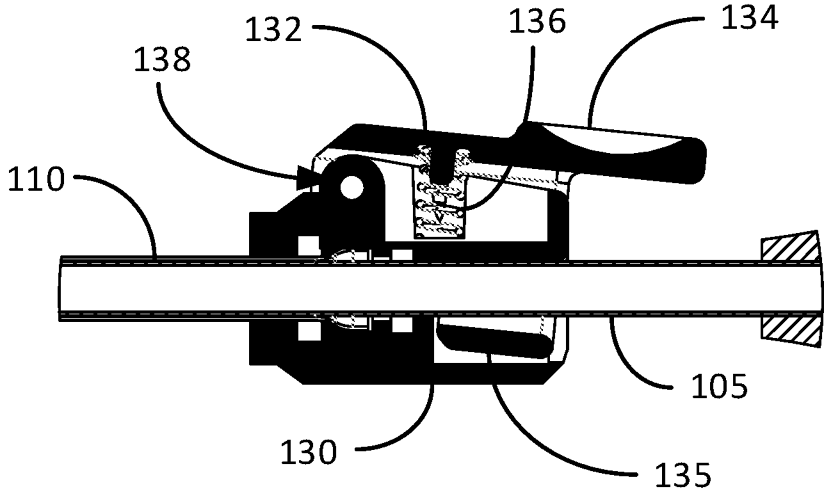

FIGS. 5A and 5B are cross-section view line drawings of the inner tube lock-and-release switch 130 along section line A-A consistent with embodiments of the present invention. FIG. 5A depicts the inner tube lock-and-release switch 130 in a locked orientation, which retains the inner tube 105 inside of the rigid outer tube 110. In this configuration, a locking tab 135 clamps down on the rigid inner tube segment 106 via the spring force from a spring 136 housed inside of the inner tube lock-and-release switch 130. The locking tab 135 uses friction to prevent the inner tube 105 from moving inside of the rigid outer tube 110. In one embodiment, the locking tab 135 is covered in a rubber to increase the friction force. As shown, a flared proximal portion 113 of the rigid outer tube 110 retains and locks the rigid outer tube 110 in the inner tube lock-and-release switch 130. For reference, the uninterrupted passageway 126 is shown extending through the hub 120.

FIG. 5B depicts the inner tube lock-and-release switch 130 in an unlocked orientation freeing the inner tube 105 to slidingly move inside of the rigid outer tube 110. As shown, the locking tab 135 is not in contact with the rigid inner tube segment 106 due to the actuator arm 132 being rotated downward about the pivot point 138, which is accomplished by pressing down on the circular depression platform 134. When in the unlocked orientation, the inner tube 105 can be slide (relative to the rigid outer tube 110) between the retracted and protracted/extended orientations.

Figure 6A:
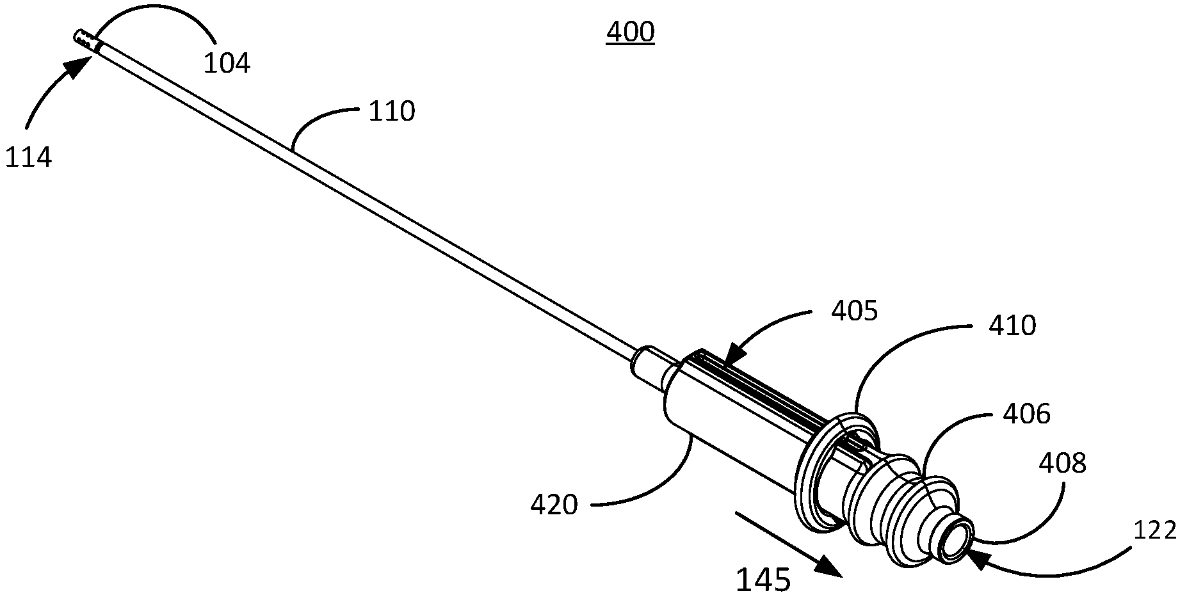
FIGS. 6A and 6B are line drawings illustratively depicting a ring actuated cannula embodiment that uses a hub ring to retract and extend the suction irrigation tip from the rigid outer tube consistent with embodiments of the present invention.
Figure 6B:
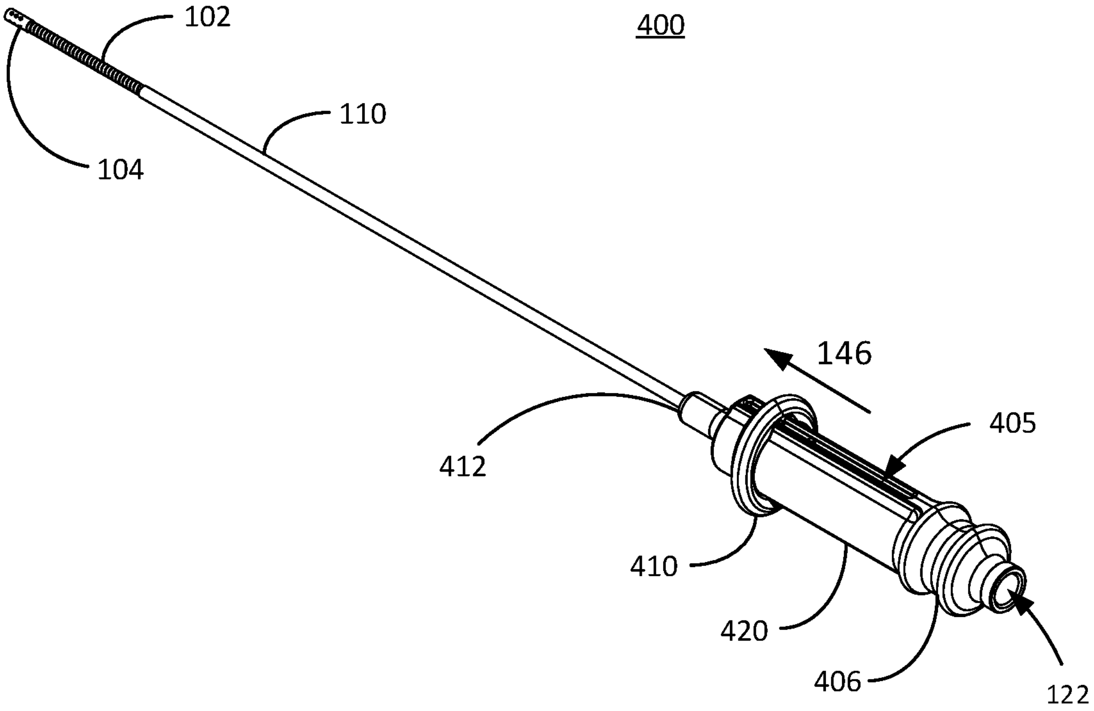

FIGS. 6A and 6B are line drawings illustratively depicting a ring actuated cannula embodiment 400 that uses a hub ring to retract and extend the suction irrigation tip from the rigid outer tube consistent with embodiments of the present invention. With greater specificity, FIG. 6A depicts the suction-irrigation tip 104 in a fully retracted orientation from the rigid outer tube 110, wherein the suction-irrigation tip 104 is pulled essentially to the rigid outer tube outlet port 114. The irrigation tip is retracted by sliding the hub ring 410 towards the hub proximal end 408, shown by the arrow direction 145. The hub ring 410 closely surrounds the hub 420, as shown, in a sliding relationship along the hub 420. The hub ring 410 is connected to the inner tube 105 by a connector arm 411 (of FIG. 8B) that extends through a hub slider slot 405 in the hub 420. Hence, by manually sliding the hub ring 410 back and forth over the hub 420, the hub ring 410 moves with the inner tube 105, and therefore retraction and extension of the suction-irrigation tip 104 from the rigid tube outlet port 114, via the connector arm 411 that extends through the slider slot 405 in the hub 420. Like the other embodiments, the hub exit port 122 is located at the hub proximal end 408. In this embodiment, the hub exit port 122 is at the hub proximal end 408 of a cylinder that extends from the finger grip 406. The cylinder facilitates a snug attachment to a drainage hose (not shown).

FIG. 6B illustratively depicts the ring actuated cannula embodiment 400 with the ring 410 slid towards the hub distal end 412 (as indicated by the arrow 146) and the suction-irrigation tip 104 in a fully extended orientation from the rigid outer tube 110. Consistent with the other embodiments disclosed herein, the flexible tube section 102 is extended from the rigid outer tube 110. In operation, the hub 420 can be held by an operator's finger and thumb at the finger grip 406 with one hand and the hub ring 410 can be manipulated back and forth along the hub 420 with the operator's other hand. The slider slot 405 and the hub exit port 122 are shown here for reference.

Figure 7A:
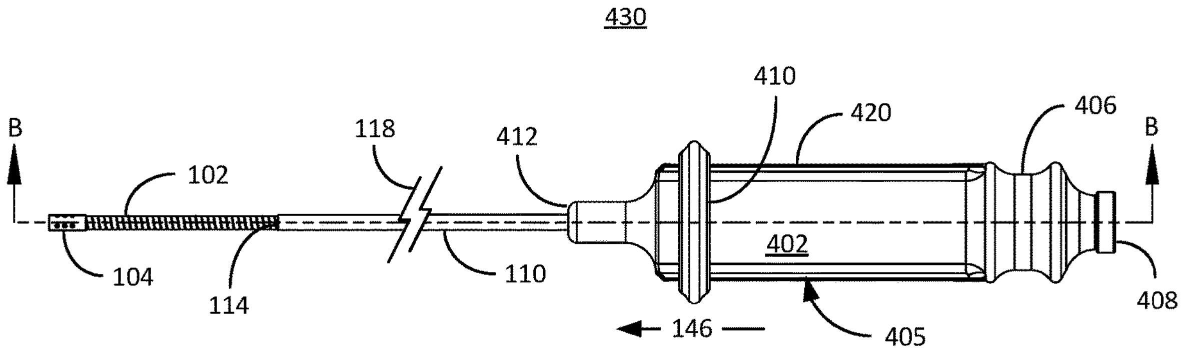
FIGS. 7A-7C are line drawings depicting the cross-section of a flexible coiled inner tube arrangement consistent with embodiments of the present invention.
Figure 7B:
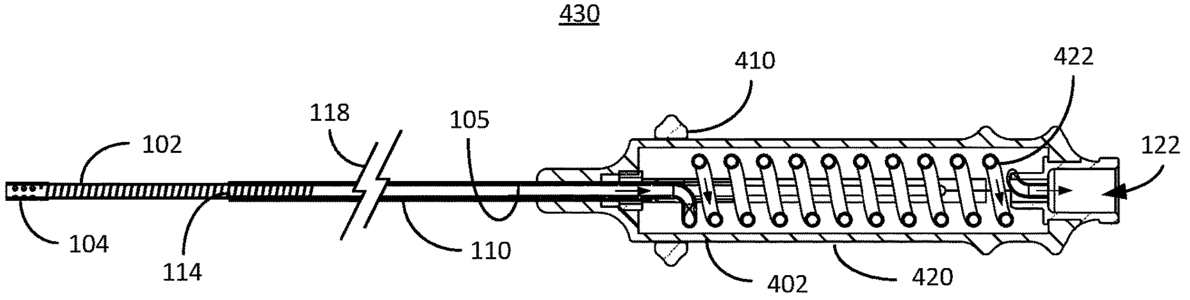
Figure 7C:
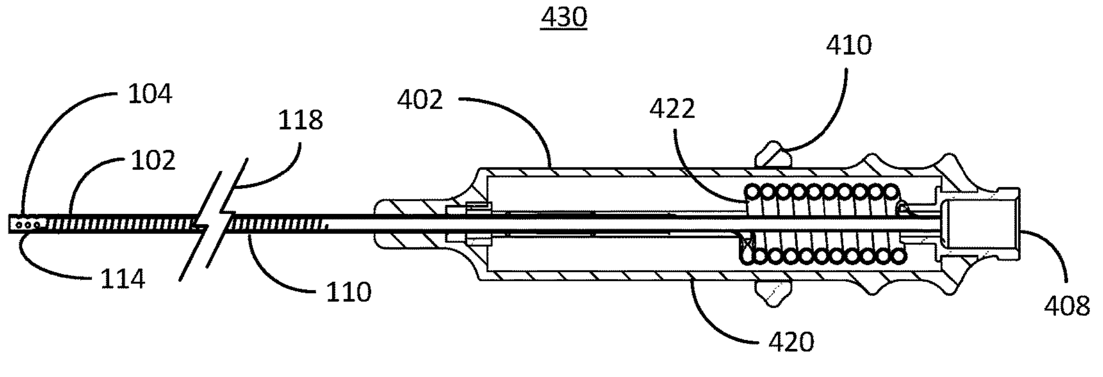

FIGS. 7A-7C are line drawings depicting the cross-section of a flexible coiled inner tube arrangement consistent with embodiments of the present invention. As shown in FIG. 7A, the flexible coiled inner tube arrangement 430, which from this outside perspective is essentially identical to the ring actuated cannula embodiment 400 of FIG. 6B, shows the suction-irrigation tip 104 in a fully extended orientation from the rigid outer tube 110. There is a cutline 118 that compresses the flexible coiled inner tube arrangement 430 along the rigid outer tube 110, as shown. The hub ring 410 is slid to the hub distal end 412, shown by the arrow 146, which corresponds to the flexible tube section 102 being deployed or otherwise extended from the rigid tube outlet port 114. In this embodiment, the hub 420 comprises two opposing slider slots 405 that penetrate through the hub housing 402 and extend linearly between the hub distal end 412 and the hub proximal end 408. In this embodiment, the slider slots 405 do not extend over the finger grip 407. A section line B-B bisects the flexible coiled inner tube arrangement 430 parallel and between the slider slots 405.

FIG. 7B illustratively depicts the cross-section of the coiled flexible inner tube arrangement 430 along section line B-B consistent with embodiments of the present invention. As shown here, the cutline 118 presents a compressed image of the flexible coiled inner tube arrangement 430 along the rigid outer tube 110 to better detail the associated elements of the arrangement 430. The suction-irrigation tip 104 and the majority of the flexible tube section 102 is extended from the rigid tube outlet port 114. In this embodiment, the inner tube 105 comprises a flexible coiled portion 422 that is coiled inside of the hub housing 402. The flexible coiled portion 422 is configured and arranged to extend and contract in response to the position of the hub ring 410 along a respective portion of the length of the hub 420. As shown by the small arrows inside of the hub 420, aspirated fluid moves through the inner tube 105, through the coiled portion 422 and out through the hub exit port 122.

FIG. 7C is a cross-section of the flexible coiled inner tube arrangement 430 of FIG. 7B but with the suction-irrigation tip 104 in a fully retracted orientation in the rigid outer tube 110. As shown here, the cutline 118 presents a compressed image of the flexible coiled inner tube arrangement 430 along the rigid outer tube 110 to better detail the associated elements of the arrangement 430. The suction-irrigation tip 104 is in a retracted orientation by the hub ring 410 being positioned along the hub 420 towards the hub proximal end 408. The flexible coiled portion 422 is compressed towards the hub proximal end 408 inside of the hub housing 402 by the hub ring 410.

Figure 8A:
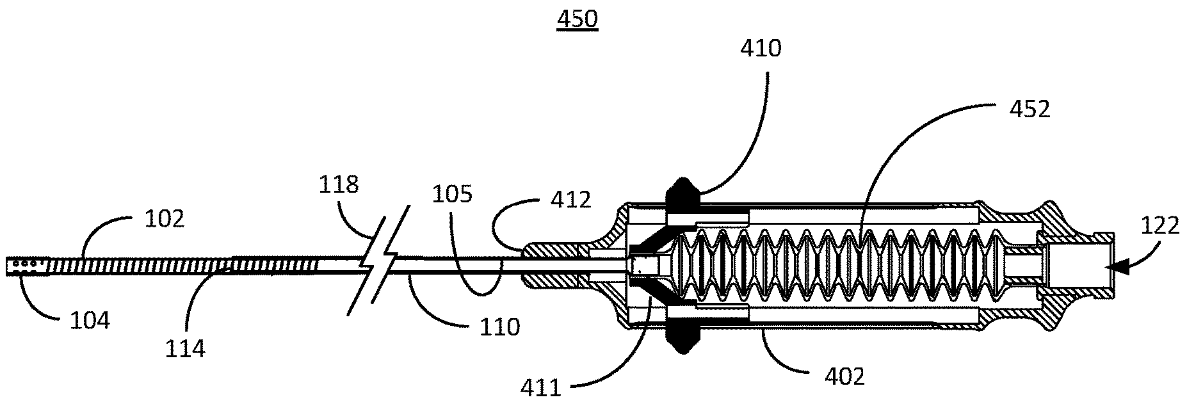
FIGS. 8A and 8B are line drawings of the cross-section of the flexible bellows arrangement consistent with embodiments of the present invention.

FIG. 8A is illustratively depicts the cross-section of the flexible bellows arrangement 450 along section line B-B of the arrangement 430 consistent with embodiments of the present invention. The outer configuration of the flexible bellows arrangement 450 of FIG. 8A looks essentially the same as the outer configuration of the arrangement 430 of FIG. 7A, hence the common use of section line B-B. As shown in FIG. 8A, the cutline 118 presents a compressed image of the flexible bellows arrangement 450 along the rigid outer tube 110 to better detail the associated elements of the arrangement 450. The suction-irrigation tip 104 and most of the flexible tube section 102 is extended from the rigid tube outlet port 114. In this embodiment, the inner tube 105 connects to a flexible bellows 452 that is stretched inside of the hub housing 402. The flexible bellows 452 is configured and arranged to extend and contract in response to the position of the hub ring 410 along a respective portion of the length of the hub 420. Aspirated fluid is intended to move through the flexible bellows 452 and out through the hub exit port 122. As shown in this embodiment, the hub ring 410 is connected to a sleeve of the distal end of the bellows 452 via a connector arm 411. The hub ring 410 is positioned towards the hub distal end 412 thereby stretching the bellows 542, as shown. As should be appreciated, the bellows 452 provides a sealed pathway to the hub exit port 122 for aspirated fluid received by the inner tube 105.

Figure 8B:
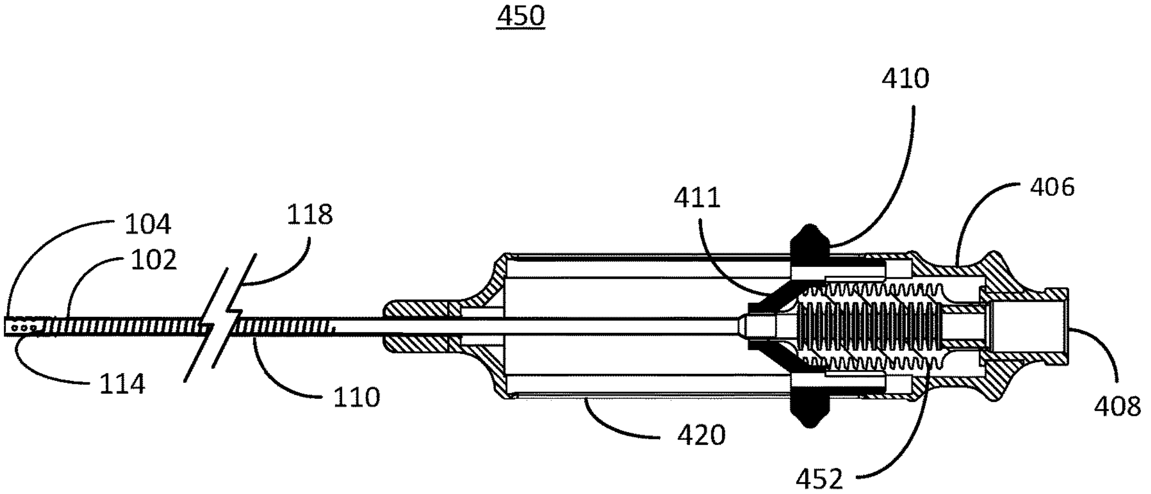

FIG. 8B is a cross-section of the flexible bellows arrangement 450 of FIG. 8B but with the suction-irrigation tip 104 in a fully retracted orientation in the rigid outer tube 110. Again, as shown here, the cutline 118 presents a compressed image of the flexible bellows arrangement 450 along the rigid outer tube 110 to better detail the associated elements of the arrangement 450. The suction-irrigation tip 104 is in a retracted orientation by the hub ring 410 being positioned on the hub 420 towards the hub proximal end 408. The bellows 452 is compressed towards the hub proximal end 408 inside of the hub housing 402 by the hub ring 410 and connector arms 411.

Figure 9A:
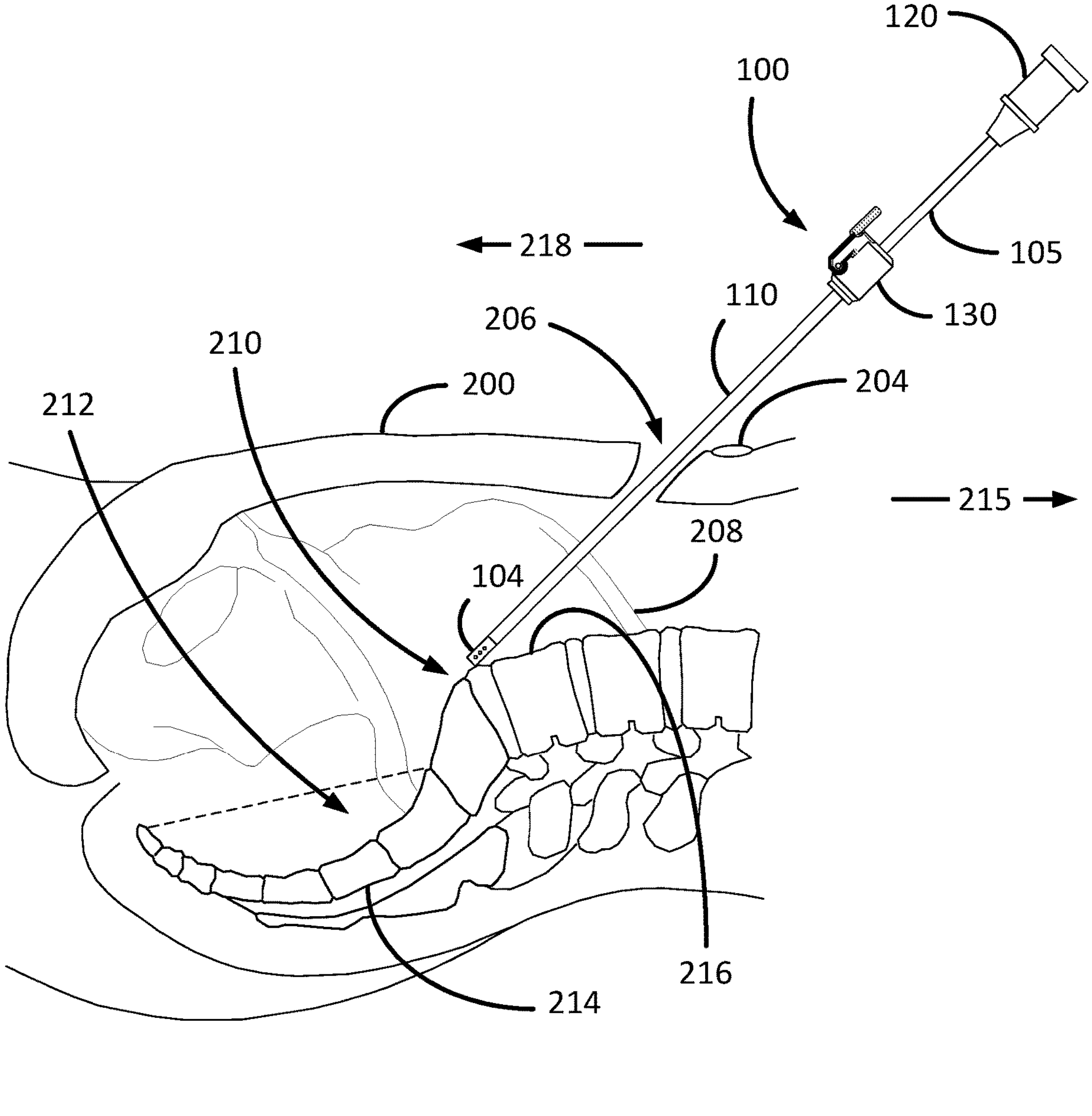
FIGS. 9A and 9B are line drawings depicting deployment of a cannula embodiment in the abdomen of a human patient consistent with embodiments of the present invention.
Figure 9B:
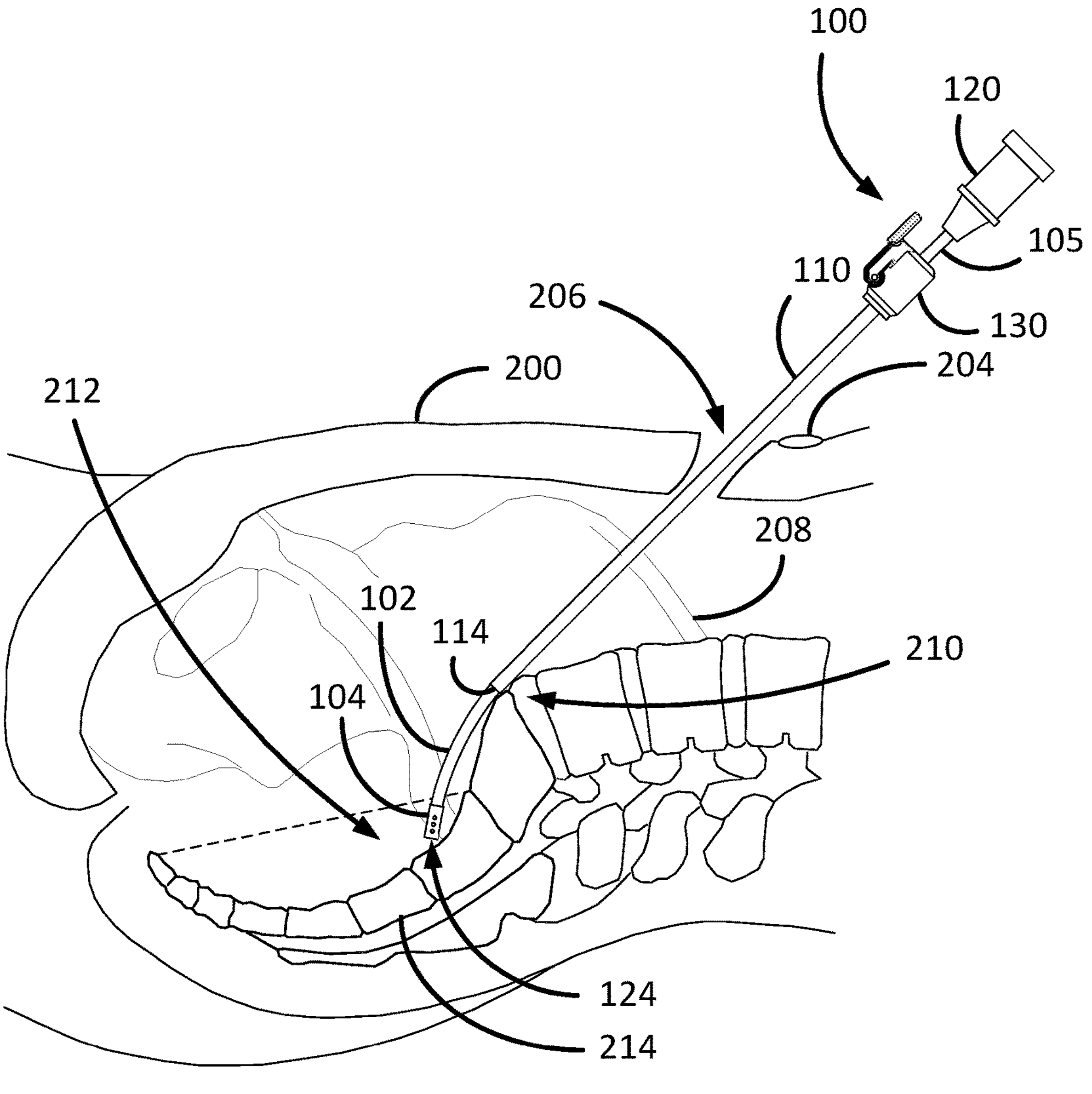
Figure 10:
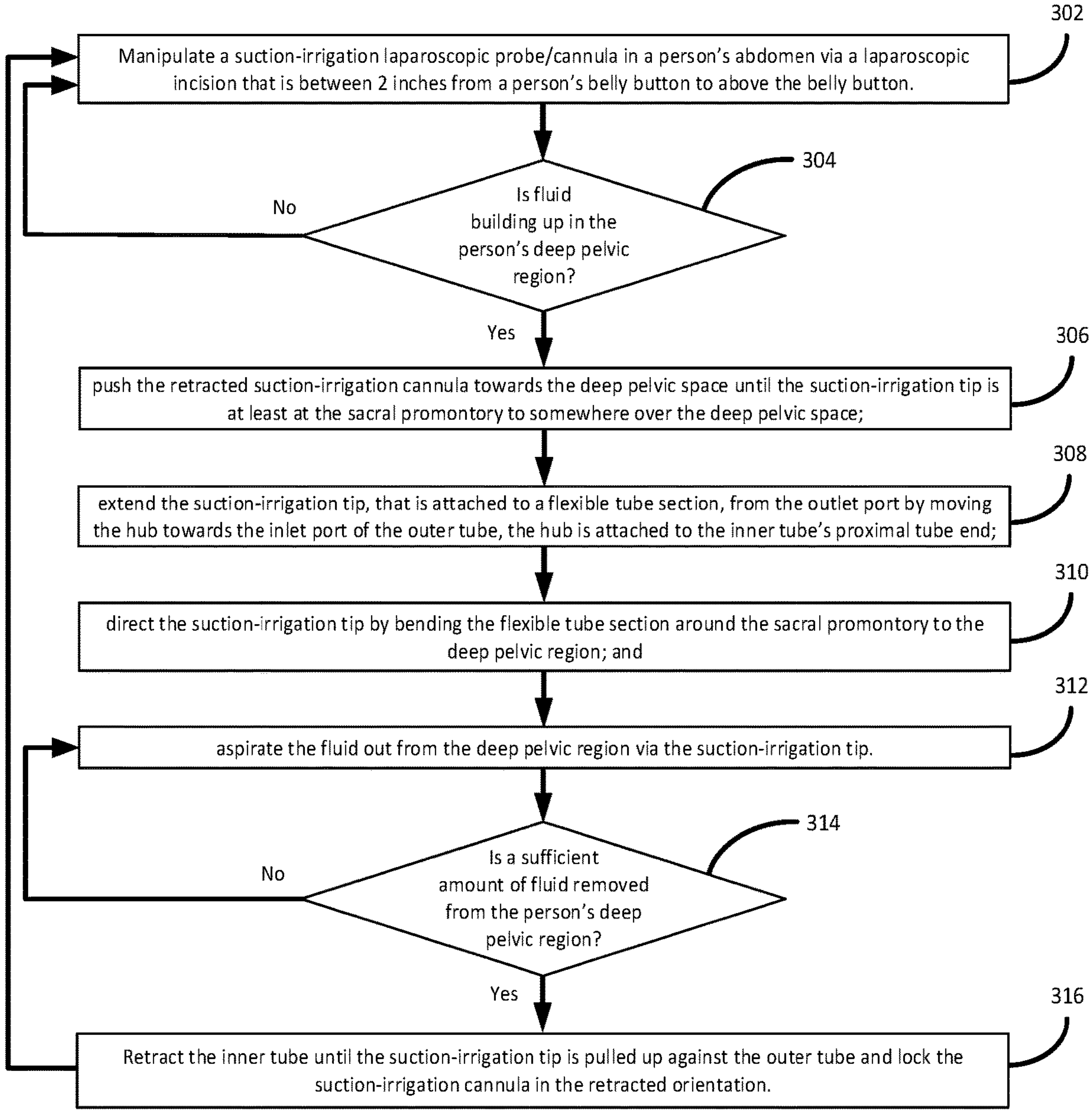
FIG. 10 is a block diagram of method steps showing a method embodiment to use the cannula embodiment.

FIGS. 9A and 9B are line drawings depicting deployment of the cannula embodiment 100 in the abdomen of a human patient consistent with embodiments of the present invention. The other cannula embodiments 400, 430 and 450 can be equally employed in the below deployment embodiment without departing from the scope and spirit of the present invention. FIG. 10 is a block diagram of method steps showing a method embodiment to use the cannula embodiment. FIG. 10 is described in view of FIGS. 9A and 9B. In place of a simple irrigation probe, insert a retracted suction-irrigation cannula/probe embodiment 100 in a human abdomen 200 via a laparoscopic incision 206 in the patient's abdomen. In some embodiments, the incision 206 is between 2 inches below the patient's navel 204 (see arrow 218 for the direction defining below, which is towards the patient's feet) to above the patient's navel 204 (see arrow 215 for the direction defining above, which for example, is typically up to two inches above the navel 204 but potentially more). The retracted suction-irrigation cannula 100 probe can be manipulated in the patient's abdomen 200 via a laparoscopic incision 206, to move organs and tissue around as needed, suck fluid, gas and tissue as well as irrigate and provide air, step 302. In FIG. 6A, the laparoscopic incision 206 is located just below the patient's navel 204, however the incision 206 can be anywhere above the patient's navel 204. As shown here, the patient 200 is lying on their back during the laparoscopic procedure. An embodiment of the retracted suction-irrigation cannula 100 is depicted in FIG. 3A. The retracted suction-irrigation cannula 100 is locked in place via the inner tube lock-and-release switch 130.

As reflected in the decision block of 304, if there is fluid buildup in the deep pelvic space 212 during the laparoscopic procedure, prepare the retracted suction-irrigation cannula 100 to drain the fluid buildup, step 306, otherwise continue the procedure with the retracted suction-irrigation cannula 100, step 302.

As reflected in step 306, the retracted suction-irrigation cannula 100 is pushed towards the deep pelvic space 212 via the incision 206, until the flexible tube section 102 is near (within a couple of inches), at or beyond the sacral promontory 210. The sacral promontory 210 blocks the extension of the flexible tube section 102 from being positioned into the deep pelvic space 212 along the central axis 115 (of FIG. 2). The sacral promontory 210 is located where the coccyx 214 meets the lumbar spine 216 in the pelvis 208.

With the flexible tube section 102 at the sacral promontory 210, the suction-irrigation cannula 100 is unlocked and the inner tube 105 is extended by pushing the hub 120 toward the inner tube lock-and-release switch 130, step 308.

As reflected in FIG. 6B and step 310, the suction-irrigation tip 104 is directed toward the deep pelvic space 212 by way of bending the flexible tube section 102 away from the central axis 115. The suction-irrigation tip 104 can simply arc towards the deep pelvic space 212 by way of gravity pulling down on the suction-irrigation tip 104. Optionally, the suction-irrigation tip 104 can be positioned by way of graspers or pliers (not shown) gripping and directing the suction-irrigation tip 104 in position. The graspers or pliers are envisioned to be used via a separate incision in the patient 200 (not shown). The present suction-irrigation cannula embodiment 100 is devoid of any internal steering mechanism, such as a wire or internal guide, rather the suction-irrigation tip 104 must be directed externally, such as by gravity or external graspers coming in from a separate incision.

Once in the deep pelvic space 212, step 312, fluid buildup can be aspirated via the suction-irrigation tip 104, which in this embodiment is by way of a distal cannula port 124 extending through the distal tip of the suction-irrigation tip 104. It should be appreciated that a suction hose (not shown) is connected to the hub 120 and in communication with the distal cannula port 124 via the hub exit port 122. It should further be appreciated that that instead of a suction hose or in combination with the suction hose, fluid can be provided through the uninterrupted passageway 126 and out through the suction-irrigation tip 104 to flush or dispense in the area of interest.

Decision step 314 questions whether enough fluid has been removed from the patient's deep pelvic region 212. If so, proceed to step 316 and with the inner tube lock-and-release switch 130 unlocked, retract the flexible tube section 102 inside of the rigid outer tube 110 by pulling on the hub 120. Return to step 302. Otherwise, continue aspirating the fluid buildup from the deep pelvic space 212 in step 312.

With the present description in mind, below are some examples of certain embodiments illustratively complementing some of the methods and apparatus embodiments discussed above and presented in the figures to aid the reader. Accordingly, the elements called out below are provided by example to aid in the understanding of the present invention and should not be considered limiting. The reader will appreciate that the below elements and configurations can be interchangeable within the scope and spirit of the present invention. The illustrative embodiments can include elements from the figures.

In that light, certain embodiments contemplate a cannula 100 (primarily in view of FIGS. 1, 2, 3A-3C) comprising a rigid outer tube 110 defined between an inlet port 112 and an outlet port 114, wherein a central axis 115 extends concentrically through the inlet port 112 and the outlet port 114. An inner tube 105, which is defined between a proximal tube end 108 and a distal tube end 109 comprises a suction-irrigation tip 104 located at the distal tube end 109 and a flexible tube section 102 interposed between the suction-irrigation tip 104 and a rigid inner tube segment 106. The rigid inner tube segment 106 extends from the flexible tube section 102 to the proximal tube end 108. The cannula 100 further comprises a hub 120 attached to the proximal tube end 108, wherein the hub 120 comprising a hub exit aperture/port 122 that is centered in the central axis 115. The hub exit port 122 is in communication with a suction-irrigation tip aperture 116 in the suction-irrigation tip 104. The inner tube 105 slidingly engaged inside of the rigid outer tube 110, wherein the suction-irrigation tip 104 and the hub 120 are never in the rigid outer tube 110.

Another embodiment of the cannula embodiment 100 envisions the distal tube end 109 always being at or distally beyond the outlet port 114 and the proximal tube end 108 always extends proximally from the inlet port 112.

The cannula embodiment 100 further envisions that the suction-irrigation tip 104 comprises a plurality of suction-irrigation tip apertures 116.

The cannula embodiment 100 further envisions the hub 120 being a handle.

The cannula embodiment 100 further envisions the hub exit port 122 being configured to receive either a suction hose or an irrigation hose.

The cannula embodiment 100 can further comprise an inner tube lock-and-release switch 130 configured to lock the inner tube 105 in place inside of the rigid outer tube 110 when in a locked orientation and release the inner tube 105 to freely slide inside of the rigid outer tube 110 when the lock-and-release switch 130 is in a released orientation. This can further be wherein the lock-and-release switch 130 is cylindrical and comprises an actuator arm 132 that moves between the locked orientation and the release orientation.

The cannula embodiment 100 further envisions the cannula 100 is a laparoscopic surgery cannula that is configured to navigate into a deep pelvic space 212 of a person 200 from an incision 206 that is abdominally located in the person 200. Abdominally located means located over the abdomen of a person 200, which is bounded by the diaphragm and the pelvis (from the lower ribs of their rib cage to their pelvic floor).

The cannula embodiment 100 further envisions the rigid outer tube 110 being metal.

The cannula embodiment 100 further envisions the suction-irrigation tip 104 being cylindrical and having an outer suction-irrigation tip diameter 142 that is equal to an outer tube diameter 144 of the rigid outer tube 110, wherein when the suction-irrigation tip 104 is in contact with the distal tube end 114, the rigid outer tube 110 and the suction-irrigation tip 104 comprise essentially a contiguous outer diameter.

The cannula embodiment 100 further envisions the flexible tube section 102 having a flexible tube length 154 and the rigid inner tube 106 having a rigid inner tube length 152, the flexible tube length 154 being less than 50% of the rigid inner tube length 152.

The cannula embodiment 100 further envisions the flexible tube section 102 having a flexible tube length 154, the flexible tube section 102 having a spiral cut 148 along the flexible tube length 154 that provides clearance 156 between tube material of the flexible tube section 102, the clearance 156 being configured to provide flexibility of the flexible tube section 102. This could further be wherein the flexible tube material 102 is made from a metallic material, and/or that a sleeve seals the spiral cut 148, or optionally wherein the inner tube 105 comprises a Teflon coating covering the flexible tube section 102 and the rigid inner tube segment 106, the Teflon coating seals the spiral cut 148.

The cannula embodiment 100 further envisions the cannula 100 being a laparoscopic surgery cannula that is configured to navigate into a deep pelvic space 212 of a person from an incision 206 within 2 inches above or below a navel 204 of the person. Other embodiments envision the incision 206 extending from somewhere that is no more than 2 inches below the navel 204 to any location that can access the deep pelvic space 212 above the navel 204. Still, while other embodiments envision the incision 206 being in any location in the person's abdomen.

The cannula embodiment 100 further envisions that no object (an object is defined herein as a solid element that does not include a liquid, gas or human tissue) is ever disposed in the inner tube 105 from the hub exit port 122.

The cannula embodiment 100 further envisions that the flexible tube section 102 is devoid of any integrated steering linkage.

Yet other embodiments of the present invention contemplate a method comprising providing a cannula 100 (primarily in view of FIGS. 1, 2, 3A-3C, 9A-9B and 10) that has a rigid outer tube 110 defined between an inlet port 112 and an outlet port 114 that sleeves over an inner tube 105 defined between a proximal tube end 108 and a distal tube end 109. The cannula 100 defines a central axis 115 centered through the inlet port 112 and the outlet port 114. The inner tube has a suction-irrigation tip 104 located at the distal tube end 109 and a flexible tube section 102 interposed between the suction-irrigation tip 104 and a rigid inner tube segment 106. The rigid inner tube segment 106 is attached to a hub 120 at the proximal tube end 108. The hub 120 comprises a hub exit port 122 that is centered in the central axis 115. While the inner tube 105 is fully retracted in the outer tube 110 with the suction-irrigation tip 104 abutting the outlet port 114, the suction-irrigation tip 104 is inserted until it reaches a sacral promontory 210 of a person 200. This is accomplished via a laparoscopic incision 206 that is in a person's abdomen, with certain embodiments contemplating between a navel 204 of the person 200 and 2 inches below the navel 204 (see FIG. 9A) or in a location above the navel 204, typically, but not limited to 2 inches above the navel 206. The method further envisions extending at least a portion of the flexible tube section 102 from the outlet port 114 by moving the hub 220 towards the inlet port 112. Next the suction-irrigation tip 104 is directed away from the central axis 115 by bending the flexible tube section 102 around the sacral promontory 210 to a deep pelvic region 212 of the person 200.

The method embodiment further envisions that after the directing step, aspirating fluid in the deep pelvic region 212 via the suction-irrigation tip 104.

The method embodiment further envisions that when the inner tube 105 is fully retracted and at the sacral promontory 210, the suction-irrigation tip 104 cannot extend into the deep pelvic region 212.

The method embodiment further envisions that after the directing step, fluid is irrigated in the deep pelvic region 212.

The method embodiment further envisions that the hub 120 comprises a hub exit port 122 that is centered along the central axis 115, the hub exit port 122 is in communication with at least one suction-irrigation tip port 116 in the suction-irrigation tip 104.

The method embodiment further envisions that the directing step is accomplished by grasping the suction-irrigation tip 104 via a grasper that is in the person via a different incision.

The method embodiment further envisions that the directing step is never accomplished with any steering mechanism accompanying the cannula 100 that coexists in the laparoscopic incision 206.

In yet another aspect of the present invention a method (primarily in view of FIGS. 1, 2, 3A-3C, 9A-9B and 10) is envisioned for deploying a cannula 100 in a person 200. The method comprising providing the cannula 100 having an inner tube 105 defined between a proximal tube end 108 and a distal tube end 109 that is slidingly engaged in a rigid outer tube 110, which is defined between an inlet port 112 and an outlet port 114. A central axis 115 is centered through the inlet port 112 and the outlet port 114. The inner tube 105 comprises a suction-irrigation tip 104 that is located at the distal tube end 109 and a flexible tube section 102 extending towards the proximal tube end 108. A hub 120 is attached to the proximal tube end 108, wherein the hub 120 comprising a hub exit port 122. The suction-irrigation tip 104 is inserted to a sacral promontory 210 of the person 200 via a laparoscopic incision 206 that is 2 inches below a navel 204 of the person 200 and all distal areas above the navel 204. During this step, the inner tube 105 is fully retracted in the outer tube 110. The suction-irrigation tip 104 abuts the outlet port 114 when the inner tube 105 is fully retracted in the outer tube 110. At least a portion of the flexible tube section 102 is extended or otherwise protracted from the outlet port 114 by pushing the hub 220 towards the inlet port 112. The suction-irrigation tip 104 is directed away from the central axis 115 either via a force external to the cannula 100 or by bending the flexible tube section 102 around the sacral promontory 210 to a deep pelvic region 212 of the person 200. When in the person, the inner tube 105 never contains material other than that consisting of gas, irrigation fluid, bodily fluid, or bodily tissue. In certain embodiments, the suction-irrigation tip 104 is cylindrical and has an outer suction-irrigation tip diameter 142 that is equal to an outer tube diameter 144 of the rigid outer tube 110.

The above sample embodiments should not be considered limiting to the scope of the invention whatsoever because many more embodiments and variations of embodiments are easily conceived within the teachings, scope and spirit of the instant specification.

It is to be understood that even though numerous characteristics and advantages of various embodiments of the present invention have been set forth in the foregoing description, together with the details of the structure and function of various embodiments of the invention, this disclosure is illustrative only, and changes may be made in detail, especially in matters of structure and arrangement of parts within the principles of the present invention to the full extent indicated by the broad general meaning of the terms in which the appended claims are expressed. For example, though the flexible tube section 102 comprises a plurality of side perforations 116, a single distal port 124 could equally be used while still maintaining substantially the same functionality without departing from the scope and spirit of the present invention. Optionally, instead of a distal port 124 only side perforations 116 can be used to aspirate or irrigate through the suction-irrigation tip 104. Another example can include providing various other locking and releasing devices without departing from the scope and spirit of the present invention. Yet another example can include various ways to move the tip when the cannula is in a protracted orientation including an add-on device or a steering device that goes into the same incision with the cannula, for example. It should further be appreciated that other locking mechanisms or deploying mechanisms including various hub arrangements (exemplified in FIGS. 6A-8B) but not specifically described can be used to deploy the cannula's inventive aspects without departing from the cannula's function and basic layout. It should be appreciated that elements of various embodiments described herein can be combined in obvious manners by a person skilled in the art that understands the content of the present specification without departing from the scope of the subject matter presented herein. Further, the term "one" is synonymous with "a", which may be a first of a plurality.

It will be clear that the present invention is well adapted to attain the ends and advantages mentioned as well as those inherent therein. While presently preferred embodiments have been described for purposes of this disclosure, numerous changes may be made which readily suggest themselves to those skilled in the art and which are encompassed in the appended claims.

What is claimed is:

1. A method comprising:

providing a cannula comprising a rigid outer tube defined between an inlet port and an outlet port that sleeves over at least a portion of an inner tube defined between a proximal tube end and a distal tube end, a central axis centered through the inlet port and the outlet port, a suction-irrigation tip located at the distal tube end and a flexible tube section interposed between the suction-irrigation tip and a rigid inner tube segment, the rigid inner tube segment is attached to a hub at the proximal tube end, the hub comprising a hub aperture that is centered along the central axis and is in communication with a suction-irrigation aperture in the suction-irrigation tip;

while the inner tube is fully retracted defined by the suction-irrigation tip abutting the outlet port, inserting the suction-irrigation tip to a sacral promontory of a person via a laparoscopic incision that is in an abdomen of the person;

extending at least a portion of the flexible tube section from the outlet port;

directing the suction-irrigation tip away from the central axis by bending the flexible tube section around the sacral promontory to a deep pelvic region of the person.

2. The method of claim 1 further comprising after the directing step, aspirating fluid in the deep pelvic region via the suction-irrigation tip, wherein the cannula solely aspirates and irrigates.

3. The method of claim 1, wherein when the inner tube is fully retracted and at the sacral promontory or beyond the sacral promontory, the suction-irrigation tip cannot extend into the deep pelvic region.

4. The method of claim 1, wherein the directing step is accomplished by grasping the suction-irrigation tip via a grasper that is in the person via a different incision.

5. The method of claim 1, wherein the directing step is never accomplished with wires or guides internal to the cannula that coexists in the laparoscopic incision.

6. The method of claim 1, wherein the inner tube is slidingly engaged in the rigid outer tube, the inner tube devoid of any other tubes therein.

7. The method of claim 1, wherein the extending step is after the inserting step and before the directing step.

8. The method of claim 1, further comprising flowing fluid through an uninterrupted passageway that starts at the distal tube end and extends through the hub aperture to a proximal end of a hose that is connected to the hub aperture.

9. The method of claim 1, wherein during the inserting step, the extending step and the directing step, the inner tube, accommodating both suction and irrigation, never contains material other than that consisting of a material composition of the inner tube, irrigation fluid, bodily fluid, gas, or bodily tissue.

10. The method of claim 1, wherein the distal tube end is always at or distally beyond the outlet port and the proximal tube end always extends proximally from the inlet port.

11. The method of claim 1, wherein the suction-irrigation tip comprises a plurality of suction-irrigation tip apertures.

12. The method of claim 1 further comprising a suction hose or an irrigation hose connected to the hub aperture.

13. The method of claim 1, wherein the flexible tube section comprises spiral cuts that are sealed by a waterproof sleeve.

14. The method of claim 1, wherein no man-made object is ever disposed in the inner tube from the hub aperture, the inner tube accommodates both suction and irrigation.

15. A method comprising:

providing a cannula comprising an inner tube defined between a proximal tube end and a distal tube end, at least a portion of the inner tube disposed inside of a rigid outer tube defined between an inlet port and an outlet port, a central axis centered through the inlet port and the outlet port, a suction-irrigation tip located at the distal tube end and a flexible tube section interposed between the suction-irrigation tip and a rigid inner tube segment, the rigid inner tube segment is connected to a hub at the proximal tube end, a hose connected to the cannula, the hose in communication with the suction-irrigation tip via the distal tube end;

while the inner tube is fully retracted defined by the suction-irrigation tip abutting the outlet port, inserting the suction-irrigation tip to a sacral promontory of a person via a laparoscopic incision that is in an abdomen of the person;

extending at least a portion of the flexible tube section from the outlet port but not extending the rigid inner tube segment from the outlet port;

directing the suction-irrigation tip away from the central axis at the sacral promontory to a deep pelvic region of the person.

16. The method of claim 15 further comprising after the directing step, aspirating fluid in the deep pelvic region through the hose via the suction-irrigation tip, the hose is connected to a hub aperture in the hub wherein the hub aperture is in liquid communication with the suction-irrigation tip.

17. The method of claim 15, wherein the suction-irrigation tip is connected to only the inner tube, only the inner tube is ever at least partially inside of the rigid outer tube.

18. The method of claim 15, wherein the directing step is never accomplished with wires or guides internal to the cannula.

19. A method comprising:

providing a cannula comprising:

a rigid outer tube defined between an inlet port and an outlet port, wherein a central axis is centered through the inlet port and the outlet port;

an inner tube defined between a proximal tube end and a distal tube end, wherein the inner tube comprising a rigid inner tube segment and a flexible inner tube segment, the flexible inner tube segment is connected to a suction irrigation tip at the distal tube end, the rigid outer tube sleeves over at least a portion of the inner tube;

a hub located at the proximal tube end, the hub comprising a hub aperture that is centered along the central axis and is in communication with a suction-irrigation aperture in the suction-irrigation tip;

while the suction-irrigation tip is abutting the outlet port, inserting the suction-irrigation tip to a sacral promontory of a person via a laparoscopic incision that is in an abdomen of the person;

extending at least a portion of the flexible inner tube segment from the outlet port;

directing the suction-irrigation tip around the sacral promontory to a deep pelvic region of the person by bending the flexible inner tube section away from the central axis;

aspirating fluid through the suction-irrigation tip from the deep pelvic region through a hose that is connected to the hub aperture.

20. The method of claim 19, wherein the hub aperture is at the proximal end of a proximal hub end of the hub, an uninterrupted passageway defined between the hub aperture and the distal tube end.

* * * * *